United States Patent

Lav

[11] Patent Number: 5,971,966
[45] Date of Patent: Oct. 26, 1999

[54] NEEDLE MAGAZINE

[75] Inventor: Steffen Lav, Broenshøj, Denmark

[73] Assignee: Novo Nordisk A/S, Bagsvaerd, Denmark

[21] Appl. No.: 08/765,760

[22] PCT Filed: Jul. 14, 1995

[86] PCT No.: PCT/DK95/00306

§ 371 Date: Jan. 8, 1997

§ 102(e) Date: Jan. 8, 1997

[87] PCT Pub. No.: WO96/02290

PCT Pub. Date: Feb. 1, 1996

[30] Foreign Application Priority Data

Jul. 19, 1994 [DK] Denmark .................. 0857/94

[51] Int. Cl.$^6$ .............. A61M 5/00; B65D 83/10
[52] U.S. Cl. ............ 604/263; 604/110; 604/192; 206/365
[58] Field of Search ................ 604/110, 263, 604/192, 198; 206/571, 367, 363–365, 368

[56] References Cited

U.S. PATENT DOCUMENTS

| | | | |
|---|---|---|---|
| 2,953,243 | 9/1960 | Roehr | 604/263 |
| 3,381,813 | 5/1968 | Coanda et al. | 206/365 |
| 4,790,827 | 12/1988 | Haber et al. | 604/263 |
| 4,874,384 | 10/1989 | Nunez | 604/263 |
| 4,927,018 | 5/1990 | Yang et al. | 206/365 |
| 4,961,730 | 10/1990 | Poncy | 604/198 |
| 4,968,304 | 11/1990 | Alter et al. | 604/198 |
| 5,127,522 | 7/1992 | Ranford | 206/363 |
| 5,154,698 | 10/1992 | Compagnucci et al. | 604/198 |
| 5,197,953 | 3/1993 | Colonna | 604/263 |
| 5,312,370 | 5/1994 | Talonn et al. | 604/197 |
| 5,393,301 | 2/1995 | Goldberg | 604/263 |

FOREIGN PATENT DOCUMENTS

| | | | |
|---|---|---|---|
| 3842317 | 6/1990 | Germany | 604/263 |
| 82/00412 | 2/1982 | WIPO . | |
| 9000073 | 1/1990 | WIPO | 604/263 |

*Primary Examiner*—Ronald K. Stright, Jr.
*Attorney, Agent, or Firm*—Steve T. Zelson, Esq.

[57] ABSTRACT

A magazine for storing and final disposal of a snap-on needle unit has a compartment having a bottom, a cylindrical side wall, and an access opening, which compartment accommodates the needle unit with a gap between the outer side wall of this needle unit and the inner side wall of the compartment. A circle of tongue-shaped protrusions are at one end thereof hinged at the inner surface of the side wall of the compartment and are at their other ends free. The length of the protrusions exceeds the width of the gap so that the protrusions are deflected to assume an oblique position with their free ends pointing towards the access opening of the compartment when the unused needle is stored in the magazine and pointing towards the bottom of the compartment when the needle unit is reinserted into the magazine.

7 Claims, 2 Drawing Sheets

NEEDLE MAGAZINE

CROSS-REFERENCE TO RELATED APPLICATIONS

This application is a 35 U.S.C. 371 national application of PCT/DK95/00306 filed Jul. 14, 1995 and claims priority under 35 U.S.C. 119 of Danish application 0857/94 filed Jul. 19, 1994, the contents of which applications are fully incorporated herein by reference.

BACKGROUND OF THE INVENTION

1. Field of Invention

The invention relates to a magazine for storing and final disposal of a snap-on needle unit carrying a needle mounted in a hub comprising a sleeve with an open end for insertion of a needle receiving part of a syringe and exhibiting a cylindric outer wall.

2. Description of Related Art

A snap-on needle unit is a unit which may be mounted on a syringe by an axial movement of the syringe and the needle unit towards each other. During this movement a needle receiving part of the syringe is passed into a sleeve of a needle hub forming part of the needle unit until protrusions on the inner surface of the sleeve engage recesses in the needle receiving part.

As opposed to needle units which a screwed onto the syringe an axial pressure must be exerted on the needle unit and the syringe to provide the snap engagement between the two parts. Correspondingly a certain axial force must be used to pull the syringe and the needle unit apart again when after use the needle is removed from the syringe for final disposal.

During mounting and dismounting of the needle unit it is important that the outer pointed end of the needle is protected so that neither the user nor an assisting person scratch himself by this pointed end. Therefore the needle unit is stored in a magazine which covers the needle unit only leaving free the opening wherein the needle receiving part of the syringe shall be inserted.

SUMMARY OF THE INVENTION

It is the object of the invention to provide a magazine which may further be used for removing a used needle from the syringe and for keeping it locked in the magazine in a position so that the used needle may not be removed from the magazine after the reinsertion therein. Further it is the object of the invention to show appropriate modifications of the needle unit design which ensures a good collaboration between the needle unit and the magazine.

A magazine according to the invention is characterized in that it has a compartment having a bottom, a cylindric side wall, and an access opening, which compartment accommodates the needle unit with a gap between the outer side wall of this needle unit and the inner side wall of the compartment, and that a circle of tongue shaped flexible protrusions at one end thereof are hinged at the inner surface of the side wall of the compartment and at their other end are free, the length of the protrusions exceeding the width of the gap so that the protrusions are deflected to assume an oblique position with their free ends abutting the cylindric outer wall of the needle unit, the free ends pointing towards the access opening of the compartment when the unused needle is stored in the magazine and pointing towards the bottom of the compartment when the needle unit is reinserted in the magazine.

When the needle unit is stored in the magazine the bottom of this magazine supports the needle hub when a needle receiving end of a syringe is pressed into the needle hub to mount this hub onto the syringe. When the needle hub is snap engaged to the syringe it may easily be drawn out of the magazine with the protrusions sliding along the cylindric outer surface of the needle hub. When a used needle unit is reinserted into the magazine the flexible protrusions will have assumed a position wherein the opening defined by the free end of the protrusion has a smaller diameter than has the cylindric part of the needle hub. When the hub is inserted the protrusions will be deflected with their free ends pointing toward the bottom of the compartment until these protrusions assume an oblique position where the cylindric part of the needle unit may pass the free ends of the protrusions which may now slide over the surface of the cylindric part during the further insertion of the needle unit into the magazine. When hereafter the syringe is retracted the protrusions will jam in the gap and retain the needle unit back in the magazine so that pulling the syringe and the magazine away from each other will result in a release of the snap engagement between the needle unit and the syringe.

Not to rely only on the jamming of the protrusions in the gap between the compartment wall and the needle unit the free end of the protrusion abutting the cylindric part of the needle unit may be sharpened so that they will cut into this cylindric part when an attempt is made to move this unit in a direction opposite the direction indicated by the protrusions.

The circle of sharp ended flexible protrusions may appropriately be provided as radially inward extending tongues in a metal ring fixed to the inner wall of the compartment of the magazine.

Due to the locking function of the protrusions the new needle units which are sold stored in the magazine may not just be inserted into the magazine as this would put the protrusion in their locking position. Therefore a special packing technique must be used to ensure that the protrusions of magazines with new needle units ready for use are pointing towards the access opening of the magazine. This may be obtained when the protrusions are provided on the inner surface of sleeve which as a lining is inserted and secured in the compartment. This construction allows that a new and unused needle unit is placed in the magazine whereafter the lining sleeve is inserted in the compartment through the access opening thereof. During the insertion of the lining the free ends of the protrusions will be deflected towards the access opening by the cylindric part of the needle unit already placed in the magazine. With this direction of the protrusions the needle unit may easily be drawn out of the magazine.

The collaboration of the locking means of the magazine and the cylindric part of the needle unit may be enhanced by appropriate design of said cylindric part. This design may consist in the provision of at least one circumferential edge on the cylindric wall of the needle unit. The edge may be drawn past the protrusions as long as these protrusions point away from the edge, but a jamming will occur when the ends of the protrusions abuts against the edge as the protrusion not only have to be deflected but must be crumbled to let the edge pass.

Such an edge may be provided by the ends of a number of circumferentially spaced axial ribs on the cylindric outer wall of the needle unit.

In another embodiment the cylindric part of the needle unit may be provided with a circumferential ring shaped protrusion to provide the circumferential edge.

In still another embodiment the circumferential edge may be provided as the edge of a circumferential recess in the cylindric part of the needle hub.

BRIEF DESCRIPTION OF THE DRAWINGS

In the following the invention is further described with reference to the drawings, wherein.

DESCRIPTION OF THE PREFERRED EMBODIMENTS

Figure 1:
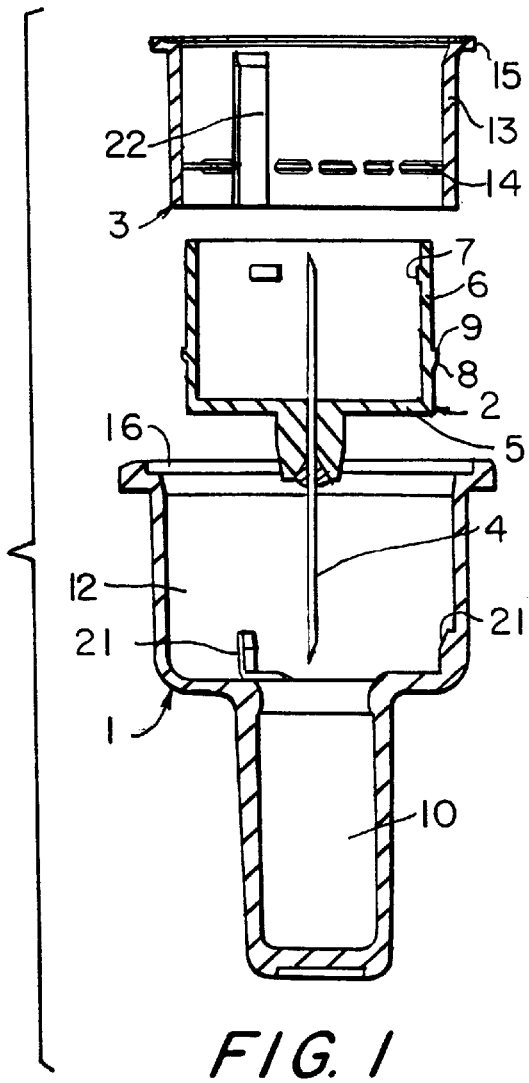
FIG. 1 shows a sectional view of a not assembled embodiment of a magazine and needle according to the invention.

In FIG. 1 is shown a magazine 1, a needle unit 2, and a locking sleeve 3 in a position ready to be assembled to store the needle unit in the magazine in a way making it possible to take the needle unit from the magazine and to reinsert the needle unit in the magazine for final disposal.

The needle unit 2 comprises an injection needle 4 carried in a needle hub comprising a bottom 5 which carries a cylindric sleeve 6 surrounding one end of the needle 4 and having at its inner surface protrusions 7 for engagement with recesses in a needle receiving part of a syringe. On its outer surface the sleeve 6 has a circumferential rib 8 exhibiting an edge 9 facing the open syringe receiving end of the sleeve.

The magazine 1 comprises a needle accommodating compartment 10, needle hub support ribs 21, and a sleeve accommodating compartment 12. The needle unit is inserted in the magazine 1 with the end of the needle not surrounded by the sleeve 6 inserted in the compartment 10 and the bottom 5 of the needle hub abutting against the needle support ribs 21. Thereby the sleeve 6 will be centered in the compartment 12 leaving a uniform gap between the outer surface of the sleeve 6 and the inner surface of the cylindric wall of the compartment 12 allowing the locking sleeve 3 to be pressed in through an open end of the compartment 12.

Figure 2:
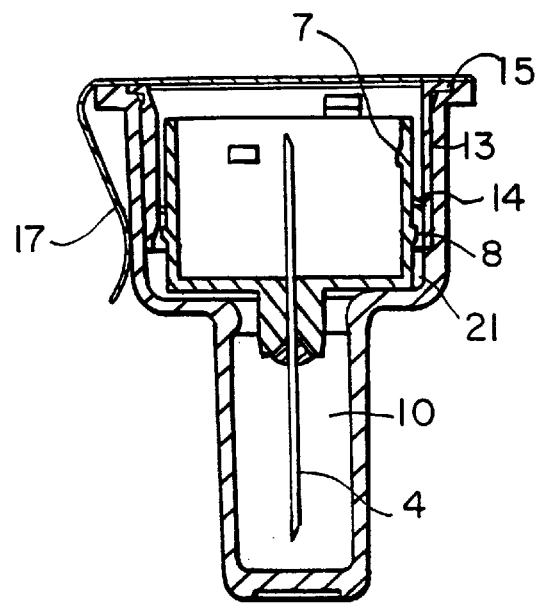
FIG. 2 shows a sectional view of the embodiment in FIG. 1 assembled for storage.

The locking sleeve 3 has a cylindrical wall 13 which is at its inner surface along a circle in a plane perpendicular to the axis of the locking sleeve 3 provided with tongue shaped projections 14 which are flexible in their connection to the inner wall of the locking sleeve 3 and which extend radially so that the circle defined by their free ends has a smaller diameter than has the needle hub. Consequently, when the locking sleeve 3 is inserted in the gap between the needle hub and the inner wall of the compartment 12 the needle hub will abut the projections 14 and deflect them to adopt an oblique position with their free ends pointing towards the open end of the magazine as shown in FIG. 2. The locking sleeve 3 is secured in the compartment 12, e.g. by having a flange 15 which is received in a recess 16 surrounding the access opening of the magazine and a gluing or welding being established between the flange 15 and the recess 16. Alternatively an irreversible snap lock connection may be provided between the outer surface of the locking sleeve and the inner cylindric surface of the compartment 12.

When the needle unit 2 is positioned in the magazine 1 and the locking sleeve is inserted in the gap between the needle hub and the magazine the magazine is closed by a membrane 17 covering the access opening of the magazine and the needle unit may in this way be maintained sterile as long as it is stored in the magazine. The membrane may be made from paper which does not allow germs to pass but is permeable to hot steam used to sterilize the needle unit in the magazine.

When the needle unit is going to be used, the membrane 17 is removed and the needle receiving part of a syringe is inserted into the open end of the sleeve 6 and moved into this sleeve until the protrusions 7 engages the recesses in the needle receiving part of the syringe. When the syringe is retracted the needle unit will follow this syringe due to the snap connection between this needle unit and the syringe. The protrusion 8 of the needle hub may pass the tongues of the locking sleeve as these tongues are passed in a direction allowing them to be further deflected. When the needle unit is removed from the magazine the tongues will due to their flexibility return to a position with their free ends defining a circle having a diameter smaller than the diameter of the needle hub.

When after use the needle hub mounted on the syringe is reinserted in the magazine the needle hub will abut the tongues and deflect them to an oblique position with their free ends pointing away from the access opening of the magazine. During further insertion of the needle unit the protrusion 8 of this unit may pass the tongues and after this passing the needle unit is locked in the magazine as a retraction will cause the free ends of the tongues to abut against the edge 9 and consequently the force exerted on the tongues during a retraction of the needle unit is not a deflecting one but a force in the longitudinal direction of the tongues so that the tongues must be crumbled before the needle unit may be removed from the magazine. For such a crumbling a force is needed which far exceeds the force needed to release the snap connection between the needle unit and the syringe, and consequently the needle unit will remain in the magazine when the syringe is retracted.

In the shown embodiment the needle unit was designed for use with the magazine by having an edge 9 facing the access opening of the magazine. This edge 9 is provided on a circumferential protrusion 8 of the needle unit. The edge may alternatively be provided as end surfaces of circumferentially spaced ribs on the outer surface of the sleeve 6 or as an edge of a circumferential recess in this outer surface.

Figure 3:
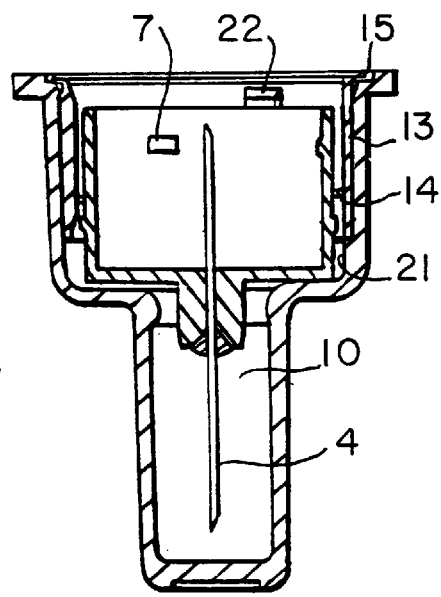
FIG. 3 shows a sectional view of the embodiment in FIG. 2 with the needle finally disposed of in the magazine.
Figure 4:
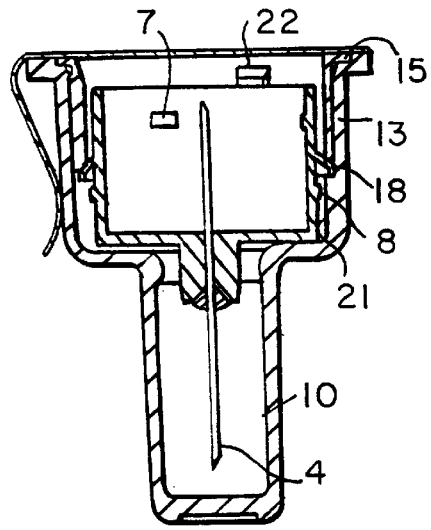
FIG. 4 shows a sectional view of another embodiment of a magazine with a stored needle unit.
Figure 5:
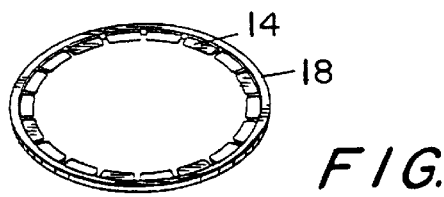
FIG. 5 shows a locking ring for the magazine shown in FIG. 4.

In a more universal embodiment of the magazine no special designed needle unit is demanded. In such an embodiment tongues 14 having a sharp free end are provided as radially inward pointing tongues of metal or a hard plastic. The locking sleeve 3 and the tongues 14 are preferably moulded as one integral part. However, if different materials are used for the sleeve and the tongues, a flat ring 18 is provided with radial inward pointing tongues 14 as shown in FIG. 5. This ring has a diameter corresponding to the diameter of the access opening of the magazine. When the needle unit is positioned in the magazine the ring is placed in the gap between the needle unit and the wall of the compartment 12 so that the needle hub deflects the tongues 14 to an oblique position with their free ends abutting the outer surface of the sleeve 6. The ring 18 is placed so it abuts a shoulder formed by ends of the needle hub supporting ribs 21 and is secured in this position by a sleeve 20 inserted from the access opening of the magazine as shown in FIG. 4. During the first removal and the reinsertion of the needle hub the tongues 14 will function in the same way as the tongues 14 in FIG. 1–3, but if an attempt is made to remove the reinserted needle unit from the magazine the sharp free end of the tongues will cut into the surface of the needle hub and provide a detent against removal of the needle unit. This function is not depending on the needle unit design and the protrusions 8 shown in FIG. 4 are not actually needed.

Figure 6:
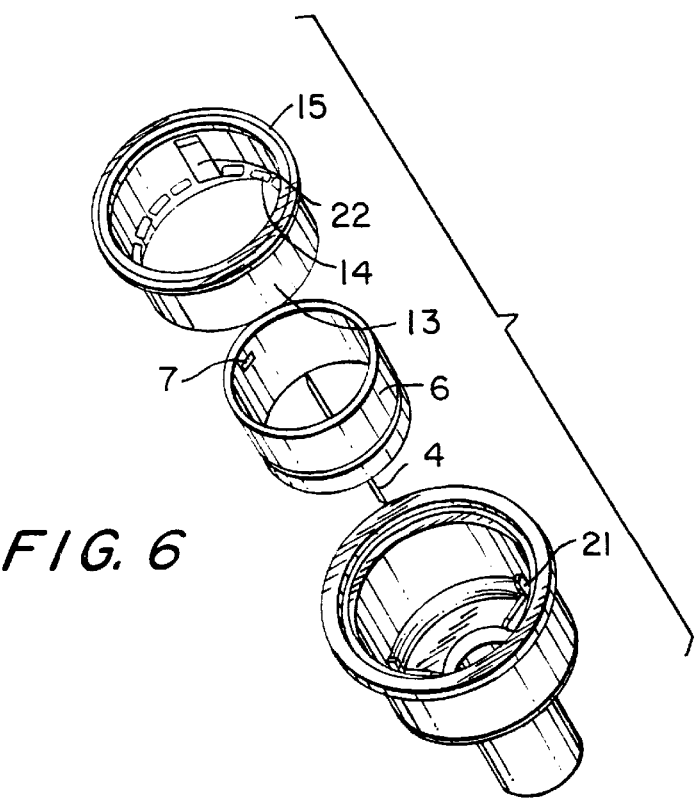
FIG. 6 shows an exploded view of an embodiment of a magazine with a needle before assembling.

FIG. 6 shows an exploded view of a magazine with a needle unit. In this figure it is seen that some of the tongues in the locking sleeve are replaced by axial guiding ribs 22 which abutting an outer circumferential surface of the needle unit contribute to the centering of the needle unit in the magazine.

I claim:

1. A single use needle assembly comprising:

a magazine having a compartment defined by a bottom, a cylindrical side wall extending in an axial direction, and an access opening;

a snap-on needle unit carrying a needle mounted in a hub, wherein said hub has an open end for insertion of a needle receiving part of a syringe, and a mainly cylindrical outer side wall, wherein said hub is disposed in the compartment and provides a gap between the hub and the compartment side wall; and at least one tongue shaped protrusion disposed in said gap, wherein said protrusion has a radially inner end and a radially outer end, wherein said radially outer end is secured to said magazine side wall, wherein said at least one protrusion extends radially inwardly from said radially outer end to hold said hub in place, and wherein said radially inner end is free to move such that said projection can be deflected in either axial direction, wherein said radially inner end lies at a distance from the axis which is less than the distance of the outer side wall of the hub from said axis such that, with the needle unit inserted in the magazine, said protrusion must assume an oblique position in the axial direction, wherein prior to using the needle unit, said radially inner end of the protrusions is deflected in a first axial direction, towards the access opening to allow the needle unit to be withdrawn from the magazine, and wherein, after the needle unit is used, reinsertion of the needle unit into the magazine causes said protrusion to deflect in an opposite axial direction, toward the bottom of the compartment; and further comprising means for effectively preventing needle reuse by opposing the withdrawal of the needle unit from the magazine when said protrusion faces said opposite direction.

2. A single use needle assembly according to claim 1, wherein the outer wall of the hub has a diameter providing an annular gap between the hub and magazine wall, and comprising a plurality of said protrusions disposed in said annular gap and having radially outer ends secured to said magazine side wall, wherein the radially inner ends of said protrusions are disposed at least generally along a circle having a diameter which is smaller than the outer diameter of the hub.

3. A single use needle assembly according to claim 2, wherein the radially inner ends of the protrusions are sharpened so as to constitute the said means for preventing needle reuse.

4. A single use needle assembly according to claims 2 or 3, comprising a sleeve disposed in said gap and secured against axial movement relative to the inner wall of the compartment, and wherein the radially outer ends of the protrusions extend from said sleeve such that said sleeve secures said radially outer ends of the protrusions to said side wall.

5. A single use needle assembly according to claim 4, wherein the cylindrical outer wall of the needle unit includes a circumferential ring-shaped protrusion providing said edge.

6. A single use needle assembly according to claim 2 or 3, further comprising a ring securing the radially outer ends of the protrusions to said side wall, wherein the ring is secured against axial movement relative to the inner wall of the compartment of the magazine.

7. A single use needle assembly according to claim 2, comprising a sleeve disposed in said gap and secured against axial movement relative to the inner wall of the compartment, wherein the radially outer ends of the protrusions extend from said sleeve such that said sleeve secures said radially outer ends of the protrusions to said side wall, wherein the outer wall of the needle hub includes at least one circumferential edge facing the open end of the sleeve and positioned axially such that, when the protrusions face said opposite direction, attempted withdrawal of the needle unit from the magazine causes the protrusion' radially inner ends to engage such edge, such that said edge forms the said means for preventing needle reuse.

* * * * *